United States Patent [19]

Woogerd

[11] Patent Number: 4,997,592

[45] Date of Patent: Mar. 5, 1991

[54] FOAMING AGENT

[75] Inventor: Stanley M. Woogerd, San Rafael, Calif.

[73] Assignee: Foam Innovations, Inc., San Jose, Calif.

[21] Appl. No.: 292,938

[22] Filed: Jan. 3, 1989

[51] Int. Cl.$^5$ .......................... B01F 17/00; B01J 13/00
[52] U.S. Cl. .................................... 252/354; 252/106; 252/307; 71/900; 71/65
[58] Field of Search ...................... 71/65, DIG. 1, 900; 252/307, 354, 106; 514/940; 424/DIG. 10, DIG. 11

[56] References Cited

U.S. PATENT DOCUMENTS

| | | | |
|---|---|---|---|
| 3,692,512 | 9/1972 | Sachnik | 71/65 |
| 3,713,404 | 1/1973 | Lavo et al. | 252/307 X |
| 4,190,427 | 2/1980 | Ravallo | 71/900 X |
| 4,325,831 | 4/1982 | Watson et al. | 252/354 |
| 4,347,145 | 8/1982 | Gregorian et al. | 252/307 x |
| 4,556,434 | 12/1985 | Woodgerd | 252/307 X |
| 4,889,654 | 12/1989 | Mason et al. | 252/106 X |
| 4,904,464 | 2/1990 | Albanese | 424/DIG. 1 X |

Primary Examiner—Richard D. Lovering
Assistant Examiner—Daniel S. Metzmaier
Attorney, Agent, or Firm—Burns, Doane, Swecker & Mathis

[57] ABSTRACT

A foaming agent for aqueous solutions including full strength solutions of herbicide, insecticide, and fungicidal formulations, liquid fertilizers, and soil funigicides, consisting essentially of the following:

| Ingredient | % wt. |
|---|---|
| 1. Sodium-2-ethyl hexyl sulfate | 19.4 |
| 2. Tetra sodium N-(1,2-dicarboxy ethyl)-N-octadecyl sulfosuccinamate | 11.0 |
| 3. Sodium dioctyl sulfosuccinate | 2.1 |
| 4. Water | 8.6 |
| 5. Isopropanol | 7.4 |
| 6. Coconut diethanolamide | 4.7 |
| 7. Triethanolamine alkylaryl sulfonate | 15.4 |
| 8. Dihexyl sodium sulfosuccinate | 31.4 |
| Total | 100.00. | each ingredient being varied by no more than ±2%.

1 Claim, No Drawings

FOAMING AGENT

This invention relates to an improved foaming agent, which is effective over a range of ±2% of chemical solutions including full strength solutions of herbicide, insecticide, and fungicide formulations, liquid fertilizer, and soil fumigants.

There are compositions which are similar, which were adapted to be compatible with a sodium metham solution. However, the present product is not soluble in or compatible with a sodium-metham-in-water solution. Instead, it has been developed to be a tank additive with superior foaming properties and is effective with a wide range of other chemical solutions.

Most pesticides in common use are complex organic compounds which, with few exceptions, are insoluble in water. In order to disperse these compounds in water to form dilute concentrations of pesticide for application, they must be dissolved in solvent together with emulsifier.

Listed below are some of the classes of solvents used in formulating organic pesticides:
  aromatic hydrocarbons (xylene, benzene, toluene, etc.);
  aliphatic hydrocarbons (kerosene, mineral spirits, etc.);
  alcohols (ethyl, methyl, isopropanol, glycerol, etc.);
  glycol ethers (methyl, ethyl, butyl etc.);
  ketones (acetone, MEK, cyclohexanone, etc.).

The classes of solvents listed above tend to be defoamers of aqueous solutions. It is important, therefore, that a pesticide foaming agent not only produces a foam that is superior for effective application but that it function in the presence of a wide variety of defoaming solvents and other agents. In addition, the foaming agent of this invention functions effectively with liquid fertilizer solutions which, because of the dissolved salts, also behave as defoamers. The foaming agent of this invention has the following formulation:

| Ingredient | % wt. |
| --- | --- |
| 1. Sodium-2-ethyl hexyl sulfate | 19.4 |
| 2. Tetra sodium N-(1,2-dicarboxy ethyl)-N-octadecyl sulfosuccinamate | 11.0 |
| 3. Sodium dioctyl sulfosuccinate | 2.1 |
| 4. Water | 8.6 |
| 5. Isopropanol | 7.4 |
| 6. Coconut diethanolamide | 4.7 |
| 7. Triethanolamine alkylaryl sulfonate | 15.4 |
| 8. Dihexyl sodium sulfosuccinate | 31.4 |
| Total | 100.00 |

The nature and purpose of the various ingredients are as follows:

1. Sodium-2-ethyl hexyl sulfate is a foaming agent which helps develop a high expansion ratio and improves the solubility of the other ingredients in the formulation.

2. Tetra sodium N-(1,2-dicarboxy ethyl)-N-octadecyl sulfosuccinamate functions as a solubilizer for mixtures of oil-soluble and water-soluble components of pesticide and fertilizer solutions, particularly when they are used in combination.

3. Sodium dioctyl sulfosuccinate is a synergist to the primary foam generator, sodium dihexyl sulfosuccinate. It improves the small bubble generation of the primary foamer and assists in foam volume generation.

4. Water is the primary solvent for the ingredients of the formulation.

5. Isopropanol is the primary co-solvent of the formulation. It reduces the viscosity of the final product and improves the miscibility upon dilution, particularly in cold temperatures.

6. Coconut diethanolamide is cationic. It provides foam stabilization and improved adhesion to negatively charged surfaces.

7. Triethanolamine alkylaryl sulfonate is a known foamer in the cosmetic industry. In this formulation, it is used as a foam booster. It also provides bubble elasticity which helps reduce the liquid drainage rate.

8. Dihexyl sodium sulfosuccinate is present in the greatest amount and is the primary small-bubble generator. Small bubbles are the best carriers of liquid in their interstitial spaces. Although this surfactant is of primary importance as a foam generator of unique quality, it is dependent upon other components of this formulation for enhancement of these properties.

Quantities of these ingredients may be varied only slightly, preferably no more than about ±2%.

The ease with which various commercial pesticide formulations can be foamed is variable within each class of pesticide as well as from class to class. This foaming agent combination has been developed in order to produce foaming applications of representative pesticide formulas from each of the classes listed above. It has been determined that the proposed foaming composition contained the optimum concentration of each component to accomplish this effect. Further, it was found that varying the ratios of the components had one or both of two effects:

1. Since the components are mutually dependent for their solubility in the whole and for the stability of the composition, variations greater than ±2% of the amount of ingredient present in the formulation may upset the solubility or stability of the composition.

2. Varying the percentages stated above may also influence the foaming performance with certain pesticide formulations.

This material is particularly useful in pesticide solutions where a foam is to be developed to enable better application of the solution in places where application is difficult.

Foams carry suspended solids better than liquids, and they reduce the problem of settling out. Foams adhere to vertical surfaces and do not run off like liquids. The residence time of foam on target areas is greater than that of liquids. The evaporation rate of foams is less, resulting in longer contact of the liquid with the target. Also, foams provide visual evidence of coverage of the chemical application.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A foaming agent for aqueous solutions including full strength solutions of herbicide, insecticide, and fungicidal formulations, liquid fertilizers, and soil fungicides, consisting essentially of the following:

| Ingredient | % wt. |
|---|---|
| 1. Sodium-2-ethyl hexyl sulfate | 19.4 |
| 2. Tetra sodium N-(1,2-dicarboxy ethyl)-N-octadecyl sulfosuccinamate | 11.0 |
| 3. Sodium dioctyl sulfosuccinate | 2.1 |
| 4. Water | 8.6 |
| 5. Isopropanol | 7.4 |
| 6. Coconut diethanolamide | 4.7 |
| 7. Triethanolamine alkylaryl sulfonate | 15.4 |
| 8. Dihexyl sodium sulfosuccinate | 31.4 |
| Total | 100.00 | wherein each ingredient is varied by no more than ±2%.

* * * * *